(12) United States Patent
Okawa et al.

(10) Patent No.: US 6,569,100 B2
(45) Date of Patent: May 27, 2003

(54) ULTRASONIC PROBE AND METHOD OF PRODUCING SAME

(75) Inventors: Eiichi Okawa, Kanagawa-ken (JP); Takashi Suzuki, Tokyo (JP); Kazuyoshi Irioka, Kanagawa-ken (JP); Jun Koizumi, Kanagawa-ken (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/990,724

(22) Filed: Nov. 14, 2001

(65) Prior Publication Data

US 2002/0062080 A1 May 23, 2002

(30) Foreign Application Priority Data

Nov. 17, 2000 (JP) ........................................ 2000-350748

(51) Int. Cl.$^7$ ................................................ A61B 8/00
(52) U.S. Cl. ...................................................... 600/445
(58) Field of Search ................................ 600/443, 447, 600/459, 460, 461, 159, 407, 146, 445; 604/95, 131

(56) References Cited

U.S. PATENT DOCUMENTS 4,567,895 A * 2/1986 Putzke ........................ 600/445
5,048,529 A * 9/1991 Blumenthal ................. 600/446
5,088,995 A * 2/1992 Packard et al. ............. 215/247
5,957,941 A * 9/1999 Ream .......................... 600/443

* cited by examiner

*Primary Examiner*—Marvin M. Lateef
*Assistant Examiner*—Maulin Patel
(74) *Attorney, Agent, or Firm*—Pearne & Gordon LLP (57) ABSTRACT

Herein disclosed is an ultrasonic probe comprising a housing, a driven shaft rotatably supported by the housing, a transducer supported by the driven shaft to be swingable on one side of the driven shaft and operative to transduce an electric signal to and from an ultrasound, a drive shaft rotatably supported by the housing spaced apart from and in parallel relationship with the driven shaft in the predetermined direction; a drive motor supported on the housing and drivably connected to the drive shaft; and a drive belt passed on the driven shaft and the drive shaft to transmit the rotation from the drive motor to the transducer. The transducer has the ultrasound emitted therefrom and reflected thereto through the housing in a predetermined direction. The ultrasonic probe thus constructed makes it possible to reduce the rotation radius of the transducer independently of the size of the electric motor by spacing the rotation axes of the drive motor and the transducer in order to provide an ultrasonic probe smaller in size. The rotation of the drive motor transferred into the rotational motion of the transducer without causing a backlash prevents the accuracy of the ultrasonic probe from deteriorating.

17 Claims, 8 Drawing Sheets

ULTRASONIC PROBE AND METHOD OF PRODUCING SAME

BACKGROUND OF THE INVENTION

1. Field of the Invention

The present invention relates to an ultrasonic probe for and a method of acquiring a tomographic image and other graphic images to be taken from the internal organs of a human body by taking advantage of an ultrasound, and more particularly to an ultrasonic probe for and a method of acquiring a tomographic image and other graphic images to be used for the diagnosis by doctors in the hospitals.

2. Description of the Related Art

In recent years, there have been developed and used various kinds of ultrasonic probes which are designed to probe the internal organs of the human body to assist the doctors in diagnosing the human body in the hospitals. Among those ultrasonic probes, there are two types of ultrasonic probes the first one of which is constructed to be moved on while being kept in touch with the human body's skin to probe the solid internal organs such as livers and pancreas from the outside of the human body, and the second one of which is inserted into the hollow internal organs of the human body including stomachs, rectums and vaginas to probe the hollow internal organs of the human body. Both of the forgoing ultrasonic probes are adapted to emit an ultrasonic wave to the targeted portions of the human body before receiving an ultrasonic wave echoed from the targeted portions of the human body. The ultrasonic wave is transformed by the ultrasonic probe in a conventional manner into an electric signal that is processed into a tomographic image to be displayed on a display unit.

One typical example of the ultrasonic probes is disclosed in Japanese publications such as for example Japanese laid-open publication No. 184532/1991.

The ultrasonic probes herein disclosed are each the second type of the ultrasonic probe and thus provided with a probe unit comprising a transducer for transducing an electric signal into and out of an ultrasonic wave, an electric motor for allowing the transducer to be reciprocally swung around its own axis within a predetermined rotation range, and a reduction gear intervening between the transducer and the electric motor to transmit the rotation torque of the electric motor to the transducer. The transducer is provided in and supported by the housing to be swingable with respect to the housing around the center axis thereof within a predetermined swing rotation range. The transducer is in the form of an arcuate shape and has a space within which the electric motor and the transducer are arranged. The electric motor and the reduction gear are positioned roughly in coaxial relationship with the transducer. The arrangement of the transducer, the electric motor and the reduction gear results in the fact that the transducer is obliged to have a relatively large radius. The large radius of the transducer inevitably makes considerably large its cross-section area taken along a plane perpendicular to the direction in which the transducer is inserted into the internal organ.

As will be understood from the previously mentioned fact, the conventional ultrasonic probe of this type encounters such a problem that the transducer relatively large in radius and cross-section makes the ultrasonic probe unit as a whole to be bulky in size. Further, the fact that the gear of the transducer is drivably meshed with the gear of the electric motor by way of the reduction gear leads to the other problem that these gears thus held in meshing relationship with one another inevitably cause a backlash transmitted to the transducer, thereby deteriorating the accuracy of the ultrasonic probe unit.

SUMMARY OF THE INVENTION

It is therefore an object of the present invention to provide an ultrasonic probe that is smaller in size than the conventional ultrasonic probe.

It is another object of the present invention to provide an ultrasonic probe that is higher in accuracy than the conventional ultrasonic probe.

It is a further object of the present invention to provide a method of producing an ultrasonic probe that is smaller in size and higher in accuracy than the conventional ultrasonic probe.

According to one aspect of the present invention, there is provided an ultrasonic probe, comprising: a housing; a driven shaft rotatably supported by the housing; a transducer supported by the driven shaft to be swingable on one side of the driven shaft and operative to transduce an electric signal to and from an ultrasound, the transducer having the ultrasound emitted therefrom and reflected thereto through the housing in a predetermined direction; a drive shaft rotatably supported by the housing, spaced apart from and in parallel relationship with the driven shaft in the predetermined direction; a drive motor supported on the housing and drivably connected to the drive shaft; and a drive belt intervening between the driven shaft and the drive shaft to transmit the rotation from the drive motor to the transducer.

The ultrasonic probe thus constructed can reduce the rotation radius of the transducer independently of the size of the electric motor by having the rotation axes of the drive motor spaced apart from the transducer. This makes it possible to produce an ultrasonic probe small in size. Further, the ultrasonic probe can be high in accuracy as compared with the conventional ultrasonic probe because the rotation of the drive motor is transferred into the rotational motion of the transducer without any gears intervening between the transducer and the drive motor.

The drive belt may be substantially in the form of a loop shape and has rectangular cross section.

The housing of the ultrasonic probe according to the present invention may include an outer case; and an inner case accommodated in the outer case and held stationary with respect to the outer case, the driven shaft being rotatably supported by the inner case; a driven pulley fixedly supported on the driven shaft of the transducer and rotatable together with the driven shaft; and a drive pulley fixedly supported on the drive shaft and rotatable together with the drive shaft, the drive belt being passed on the driven pulley and the drive pulley.

The ultrasonic probe according to the present invention desirably comprises synchronizing means for synchronizing the driven pulley with the drive pulley when the driven pulley is driven to rotate by the drive pulley through the drive belt.

It is desirable that the synchronizing means be constituted by a first projection formed on the driven pulley to radially project from the outer peripheral surface of the driven pulley, a second projection formed on the drive pulley to radially project from the outer peripheral surface of the drive pulley, and the drive belt respectively having first and second holes formed therein in spaced apart relationship with each other in the rotation direction of the drive belt, the first and second holes respectively having the first and second projections received therein to ensure that the drive pulley is driven to rotate in synchronism with the drive pulley.

The synchronizing means makes it possible to produce an ultrasonic probe with no slip causing between the drive belt and the driven and drive pulleys and thus highly responsive and reliable in the torque transmission between the drive and driven pulleys.

The ultrasonic probe according to the present invention may further comprise length adjusting means for adjusting the length of the drive belt with the first pulley and the second pulley to have the first projection and the second projections respectively engaged with first hole and the second hole. In this case, the drive belt has a predetermined length defined by the distance between the first hole and the second hole.

The ultrasonic probe according to the present invention may further comprise an adjusting screw, the drive belt has a first engaging portion held in engagement with the drive pulley, a second engaging portion held in engagement with the driven pulley and a third engaging portion held in engagement with the drive pulley and formed with an adjusting hole having an inner diameter large enough to receive therein the adjusting screw to ensure that the drive belt is adjusted in length under the state that the first engaging portion and the second engaging portion are respectively held in engagement with the drive pulley and the driven pulley.

The length adjusting means is preferably constituted by the adjusting screw, the drive belt, the drive pulley and the driven pulley. The adjusting hole may be in the form of a rectangular shape having a length measured in the longitudinal direction of the drive belt and a width measured in the direction perpendicular to the longitudinal direction of the drive belt. The length of the adjusting hole is necessary to be larger than the width.

The length adjusting means renders it possible to impart tension to the drive belt by puling the extreme end portion of the drive belt. The extreme end portion of the drive belt which falls into being unnecessary after being pulled is cut off from the effective portions of the drive belt. It is therefore possible to provide an ultrasonic probe reduced in manufacturing costs and processes because the fact that the drive belt is in the form of a loop shape.

The drive belt may have an extreme end tab adjacent to the adjusting hole and may be formed with a pair of side notches extending inwardly from the side surfaces of the drive belt between the adjusting hole and the extreme end tab of the drive belt and symmetrically formed with respect to the center line of the drive belt. The drive belt wound onto the drive pulley and the driven pulley is adjusted in length between the drive and driven pulleys with the adjusting hole and the adjusting screw and is imparted a tension by pulling the extreme end tab in the longitudinal direction of the drive belt until the third engaging portion of the drive belt is screwed to the drive pulley.

The ultrasonic probe according to the present invention may further comprise rotation restricting means for restricting the rotation of the drive pulley to within an allowable rotation range.

It is desirable that the drive pulley have a stop projection projecting from one side surface of the drive pulley. In this case, the inner case is formed with a groove receiving therein the stop projection to ensure that the drive pulley is allowed to rotate within the allowable rotation range.

Preferably, the outer diameter of the driven pulley is larger than that of the drive pulley. The load torque of the drive motor and the backlash transmitted to the transducer are therefore reduced, and the drive motor and the drive pulley become smaller.

The rotation of the drive pulley is restricted by the inner case through the stop projection of the drive pulley in the case when the transducer is brought out of the allowable rotational range of the transducer in trouble. It is therefore possible to provide an ultrasonic probe sufficiently reliable by preventing the drive belt from being applied a driving force exceeding the allowable force level.

It is preferred that the ultrasonic probe further comprise tension imparting means for imparting tension to the drive belt. The tension imparting means enables the drive belt to be imparted a constant tension sufficient to drive the transducer without loosening the drive belt and making a vibration noise.

The tension imparting means may comprise a swingable arm having one end portion pivotably supported on the inner case to be swingable with respect to the inner case and the other end portion bent toward the drive belt, an idler roller rotatably supported on the other end portion of the swingable arm in pressing contact with the drive belt, and resilient means for resiliently urging the idler roller into pressing contact with the drive belt to have the drive belt maintained under its tensioned state.

In the preferred ultrasonic probe, the resilient means is constituted by a helical coil spring having one end connected to the longitudinally intermediate portion of the swingable arm and the other end connected to the inner case to ensure that the idler roller is held in pressing contact with the drive belt to have the drive belt maintained under its tensioned state. The drive belt while being driven by the drive pulley is constantly imparted a tension at a tension level applied when the drive belt is assembled with the first and second pulleys.

According to another aspect of the present invention, there is provided a method of producing an ultrasonic probe, comprising the steps of: preparing a driven shaft, a transducer supported by the driven shaft, a drive shaft parallel to the driven shaft and spaced apart from the drive shaft, an adjusting screw and a drive belt having first and second engaging portions, third engaging portion formed with an adjusting hole and an extreme end tab; winding the drive belt onto the drive pulley and the driven pulley to have the first and second engaging portions held in engagement with the drive pulley and the driven pulley; screwing the drive belt to the drive pulley by the adjusting screw through the adjusting hole of the drive belt; imparting the drive belt wound onto the drive pulley and the driven pulley a tension at a predetermined level by pulling the extreme end tab in the longitudinal direction of the drive belt until the third engaging portion of the drive belt is screwed to the drive pulley; and cutting and separating the extreme end tab from the drive belt.

The above series of steps not only make it easy to impart tension to the drive belt but also render it possible to reduce the manufacturing costs and the number of the manufacturing processes of the ultrasonic probe because the drive belt can be tightened without providing additional tension imparting means.

BRIEF DESCRIPTION OF THE DRAWINGS

The features and advantages of the ultrasonic probe according to the present invention will more clearly be understood from the following description taken in conjunction with the accompanying drawings in which.

DESCRIPTION OF THE PREFERRED EMBODIMENTS

Figure 1A:
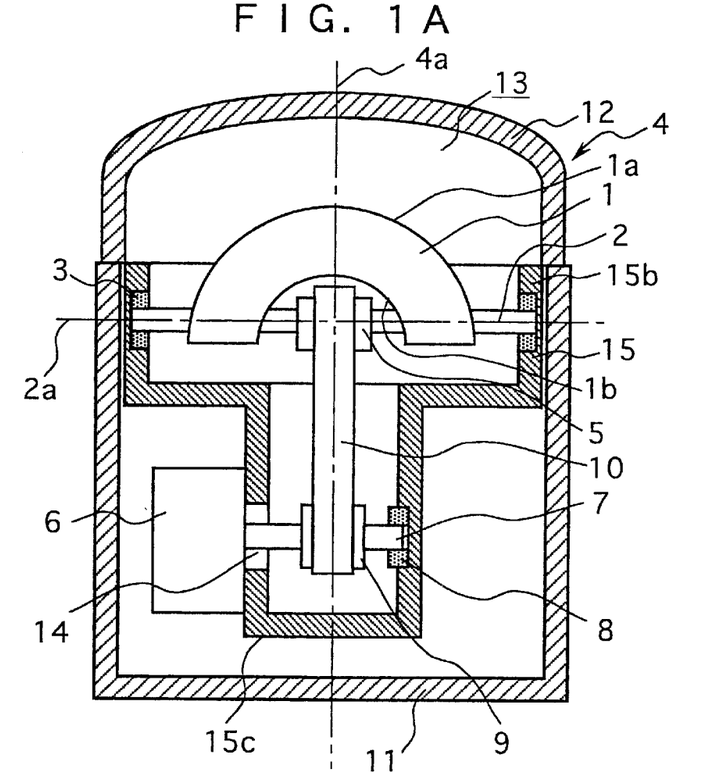
FIG. 1A is a cross-sectional view of a first embodiment of the ultrasonic probe according to the present invention.
Figure 1B:
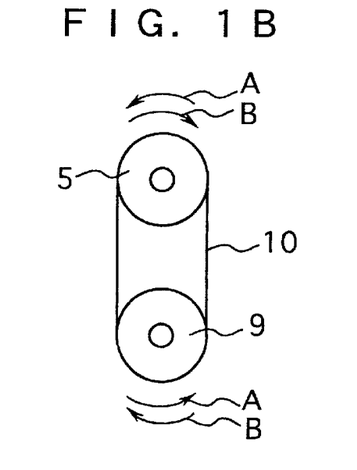
FIG. 1B is a schematic side view of a loop belt and drive and driven pulleys forming part of the first embodiment of the ultrasonic probe according to the present invention.

Referring to FIGS. 1A and 1B of the drawings, there is shown a first preferred embodiment of the ultrasonic probe embodying the present invention. The ultrasonic probe thus shown in FIGS. 1A and 1B as comprises a transducer 1, a driven shaft 2, a pair of bearings 3, a housing 4, a driven pulley 5, a drive motor 6, a drive shaft 7. The housing 4 has a center axis 4a and comprises an outer case 11, and an inner case 15 accommodated in the outer case 11 and held stationary with respect to the outer case 11. The inner case 15 is in the form of a cup shape, having an upper portion 15b connected to the outer case 11 and a lower portion 15c integrally formed with the upper portion 15b. The cross-sectional area of the lower portion 15c measured in the direction perpendicular to the center axis 4a of the housing 4 is smaller than the cross-sectional area of the upper portion 15b also measured in the direction perpendicular to the center axis 4a of the housing 4. The window member 12 is made of a material which facilitates the ultrasonic wave to pass therethrough.

The transducer 1 is drivably connected with the driven shaft 2 which is rotatably supported by the inner case 15 to extend in a predetermined direction with respect to the inner case 15. The transducer 1 is in the form of an arcuate shape and having a convex surface 1a and a concave surface 1b, the convex surface 1a leading the concave surface 1b in an ultrasound emitting direction in which the ultrasound is emitted from the transducer 1 to the targeted portion of the human body, viz., an ultrasound wave propagation direction radially extending from the central point of the driven shaft 2 at which the center axis 4a of the housing 4 is crossed with the center axis 2a of the driven shaft 2. The transducer 1 is swingable on one side of the driven shaft 2 and operative to transduce an electric signal to and from an ultrasound. The ultrasound is emitted from the transducer 1 and reflected as an ultrasonic echo by the human body.

The bearings 3 intervening between the driven shaft 2 and the inner case 15 are axially aligned and spaced relationship with each other. The driven shaft 2 is not axially slidable but rotatable about the axis of the bearing 3. The drive shaft 7 is rotatably supported by the outer case 11 in spaced-apart and parallel relationship with the driven shaft 2 in the predetermined direction.

The ultrasonic probe further comprises a driven pulley 5 fixedly supported on the driven shaft 2 of the transducer 1 and rotatable together with the driven shaft 2, and a drive pulley 9 fixedly supported on the drive shaft 7 and rotatable together with the drive shaft 7.

The ultrasonic probe further comprises an electric drive motor 6, e.g. a stepping motor supported on the housing 4 through the inner case 15 and drivably connected to the drive shaft 7, and a drive belt 10 intervening between the driven shaft 2 and the drive shaft 7 to transmit rotation from the drive motor 6 to the transducer 1. The drive shaft 7 is integrally formed with the output shaft of the drive motor 6 which is securely mounted on the lower portion 15c of the inner case 15. According to the present invention, the drive shaft 7 and the drive motor 6 may be arranged in such a way that the drive shaft 7 is separated from the drive motor 6 and drivably connected to the output shaft of the drive motor 6.

The transmission of the rotation from the drive motor 6 to the transducer 1 is realized between the drive shaft 7 and the drive belt 10 with a drive pulley 9 and a driven pulley 5. The drive pulley 9 is supported on the center portion of the drive shaft 7 and rotatable together with the drive shaft 7, while the driven pulley 5 is supported on the center portion of the driven shaft 2 of the transducer 1 and rotatable together with the driven shaft 2. As will be best shown in FIG. 1B, the drive belt 10 is in the form of a loop shape, i.e., substantially looped and passed on the driven pulley 5 and drive pulley 9. This drive belt 10 is formed into a flat strip having a rectangular cross section.

The transducer 1 is operative not only to transduce an electric signal to an ultrasound to be emitted therefrom through the window member 12 in a predetermined detecting direction but also to transduce an ultrasonic echo, i.e., a reflected ultrasound to an electric signal to be transferred into a diagnostic image. The ultrasound emitted from the transducer 1 and the ultrasonic echo reflected from the outside are transmitted through the window member 12. Between the window member 12 and the inner case 15, there is provided a liquidized ultrasonically transmissible material 13 filling up the space defined between the window member 12 and the inner case 15.

Around the drive shaft 7, there are provided a bearing 8 and a seal ring 14 each intervening between the drive shaft 7 and the inner case 15. The seal ring 14 is adapted to seal the gap between the drive shaft 7 and the outer case 11 in order to prevent the ultrasonically transmissible material 13 from leaking out of the inner case 15.

The description is now directed to the operation of the ultrasonic probe according to the present invention.

The drive motor 6 of the ultrasonic probe is at first energized to rotate the drive pulley 9 in a direction indicated by an arrow A in FIG. 1B. When the drive pulley 9 rotates in the direction A, the driven pulley 5 is driven to rotate in the direction A by the drive pulley 9 through the drive belt 10. When, on the other hand, the drive pulley 9 rotates in a direction indicated by an arrow B in FIG. 1B, the driven pulley 5 is driven to rotate in the direction B by the drive pulley 9 through the drive belt 10. The transducer 1 is then rotated back and forth to be swingable with the driven shaft 2 in an allowable rotation range. The allowable rotation range of the transducer 1 is restricted in proportion to the rotation range of the drive motor 6.

The rotation radius of the transducer 1 is reduced to be independently of the size of the drive motor 6 due to the fact that the rotation axes of the drive motor 6 and the drive shaft 7 are spaced apart from the rotation axis of the transducer 1 in the predetermined direction to be positioned on the other side of the transducer 1. The ultrasonic probe is therefore prevented from becoming bulky in size and is therefore possible to become smaller than the conventional ultrasonic probe. Further, the transducer 1 is rotated by the drive motor 6 through the drive belt 10 without using gears obliged to incur a backlash. Consequently, the ultrasonic probe is prevented from deteriorating in probing accuracy.

Figure 2:
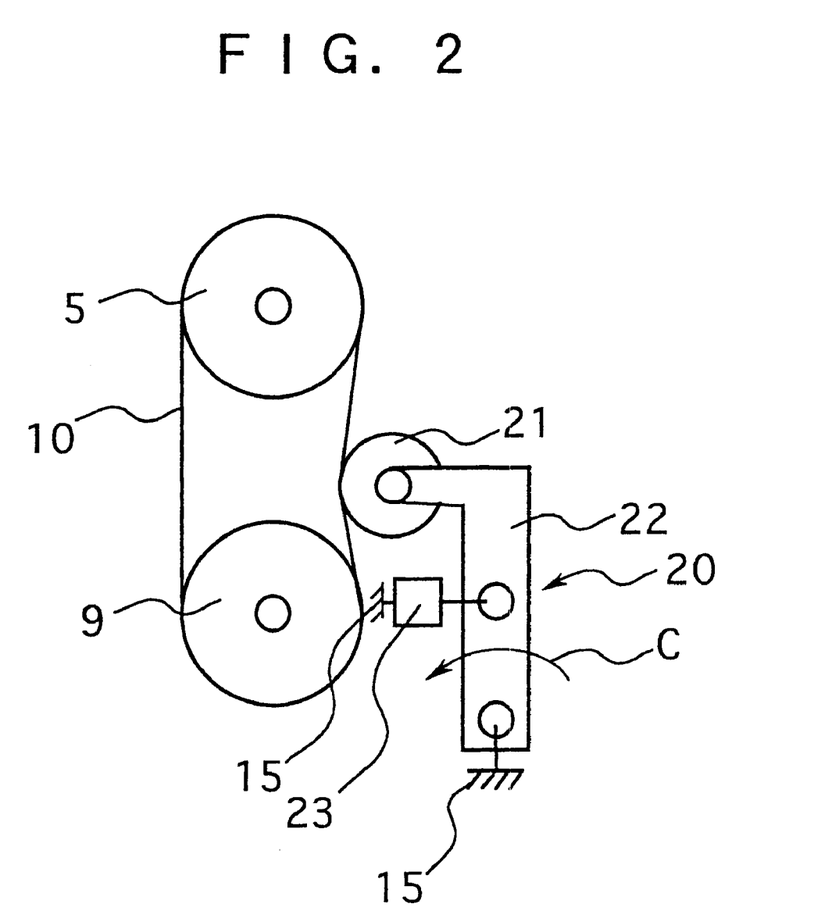
FIG. 2 is a schematic side view of tension imparting means forming part of the second embodiment of the ultrasonic probe according to the present invention.

Referring now to FIG. 2 of the drawings, there is shown a second preferred embodiment of the ultrasonic probe embodying the present invention. The ultrasonic probe of the present embodiment is similar in constitution to the first embodiment and thus includes elements the same in constitution and numerical reference as those of the ultrasonic probe of the first embodiment.

In FIG. 2, the driven pulley 5, the drive pulley 9 and the drive belt 10 constitute a rotation transmission mechanism forming part of the ultrasonic probe according to the present invention. The ultrasonic probe further comprises tension imparting means 20 for imparting the drive belt 10 a tension at a constant tension level. The tension imparting means 20 comprises a swingable arm 22 having one end portion pivotably supported on the inner case 15 to be swingable with respect to the inner case 15, an idler roller 21 rotatably supported on the other end portion of the swingable arm 22, and resilient means 23 for resiliently urging the idler roller 21 into pressing contact with the drive belt 10 to have the drive belt 10 maintained under its tensioned state. The other end portion of the swingable arm 22 is bent toward the drive belt 10 so that the idler roller 21 is rollable or slidable with respect to the outer surface of the drive belt 10.

The resilient means 23 is in constituted by a helical coil spring having one end connected to the longitudinally intermediate portion of the swingable arm 22 and the other end connected to the inner case 15 to ensure that the idler roller 21 is held in pressing contact with the drive belt 10 and that the drive belt 10 is maintained under its tensioned state.

The constant tension level of the drive belt 10 is so predetermined as to be sufficient to drive the transducer 1 through the drive belt 10 without making a vibration noise. This means that the drive belt 10 is imparted a tension so as to prevent the slip, i.e. a relative rotation between the driven pulley 5 and the drive pulley 9.

Figure 3:
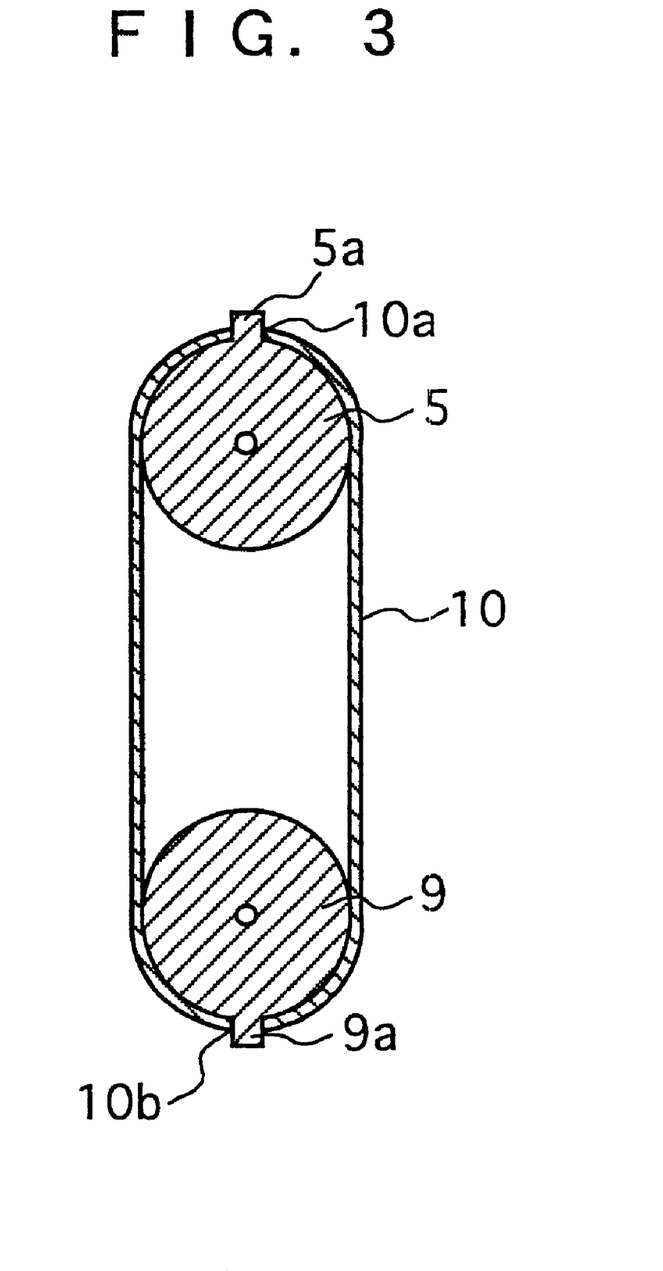
FIG. 3 is a cross-sectional side view similar to FIG. 2 but showing a loop belt and drive and driven pulleys forming part of the third embodiment of the ultrasonic probe according to the present invention.

Referring to FIG. 3 of the drawings, there is shown a third preferred embodiment of the ultrasonic probe embodying the present invention. The ultrasonic probe of the present embodiment is similar in constitution to the first embodiment and thus includes elements the same in constitution and numerical reference as those of the ultrasonic probe of the first embodiment.

The ultrasonic probe of the present embodiment comprises synchronizing means for synchronizing the driven pulley 5 with the drive pulley 9 when the driven pulley 5 is driven to rotate by the drive pulley 9 and the drive motor 6 through the drive belt 10. The synchronizing means is constituted by a first projection 5a formed on the driven pulley 5, a second projection 9a formed on the drive pulley 9, and the drive belt 10 having a first hole 10a and a second hole 10b.

The first projection 5a radially projecting from the outer peripheral surface of the driven pulley 5 is received in the first hole 10a of the drive belt 10 to have the drive belt 10 held in synchronized engagement with the driven pulley 5, while the second projection 9a radially projecting from the outer peripheral surface of the drive pulley 9 is received in the second hole 10b of the drive belt 10 to have the drive belt 10 held in synchronized engagement with the drive pulley 9. The driven pulley 5 is therefore ensured to be driven to rotate in synchronism with the drive pulley 9 without causing a slip between the drive belt 10 and the driven and drive pulleys 5 and 9. Accordingly, the ultrasonic probe becomes more reliable and accurate.

Figure 4A:
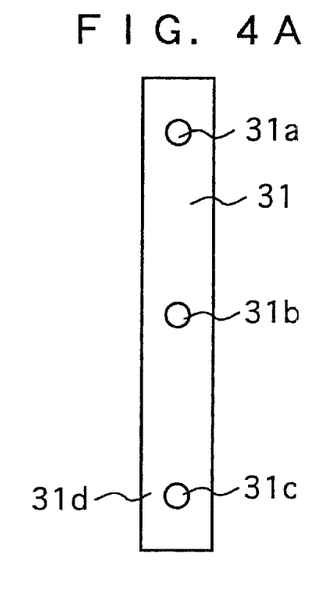
FIG. 4A is a plan view of a drive belt forming part of the fourth embodiment of the ultrasonic probe according to the present invention.
Figure 4B:
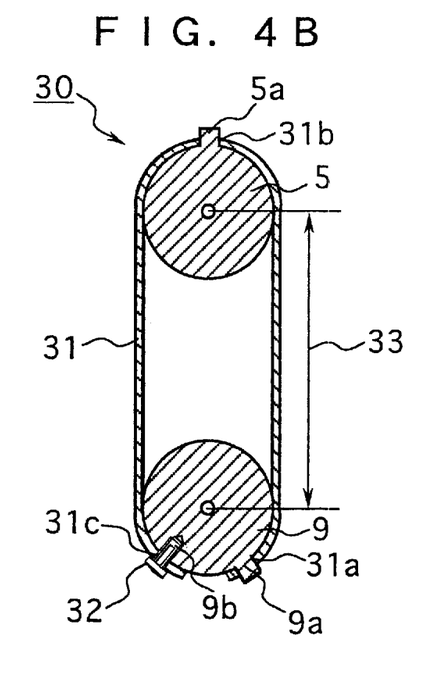
FIG. 4B is a cross-sectional side view similar to FIG. 2 but showing a loop belt and drive and driven pulleys forming part of the fourth embodiment of the ultrasonic probe according to the present invention.

Referring to FIGS. 4A and 4B of the drawings, there is shown a forth preferred embodiment of the ultrasonic probe embodying the present invention. The ultrasonic probe of the present embodiment is similar in constitution to the first and third embodiments and thus includes elements the same in constitution and numerical reference as those of the ultrasonic probe of the first embodiment.

As shown in FIGS. 4A and 4B, the ultrasonic probe comprises length adjusting means 30 for adjusting length 33 of each straightened portion of the drive belt 31, i.e. the distance between the driven pulley 5 and the drive pulley 9, with the first pulley 5 and the second pulley 9. The ultrasonic probe further comprises an adjusting screw 32. The drive belt 31 has a first engaging portion 31b held in engagement with the drive pulley 9, a second engaging portion 31a held in engagement with the driven pulley 5 and a third engaging portion 31d held in engagement with the drive pulley 9 and formed with an adjusting hole 31c. The adjusting hole 31c has an inner diameter large enough to receive therein the adjusting screw 32 to ensure that the drive belt 31 is adjusted in length under the state that the first engaging portion 31b and the second engaging portion 31a are respectively held in engagement with the drive pulley 9 and the driven pulley 5. The length adjusting means is constituted by the adjusting screw 32, the drive belt 31, the drive pulley 9 and the driven pulley 5.

The drive belt 31 is formed with a first hole 31c, a second hole 31a, and an adjusting hole 31c. The driven pulley 5 has a first projection 5a received in the first hole 31b of the drive belt 31 to have the drive belt 31 wound onto and held in synchronized engagement with the driven pulley 5. The drive pulley 9 has a second projection 9a received in the second hole 31a of the drive belt 31 to have the drive belt 31 wound onto and held in synchronized engagement with the drive pulley 9. The length adjusting means 30 is further constituted by a female screw 9b formed with the drive pulley 9 to radially extend, and an adjusting screw 32 operable to screw into the female screw of the drive pulley 9. According to the present invention, the drive pulley 9 may have a plurality of female screws formed therein to be spaced apart from one another in the circumferential direction of the drive pulley 9. The distances between the central points of the female screws may be variable in the circumferential direction of the drive pulley 9 to facilitate the length adjustment of the drive pulley 9.

As will be seen from the foregoing description, it will be understood that the first hole 31b and the second hole 31a of the drive belt 31 respectively constitute first and second engaging portions held in engagement with the drive pulley 9 and the driven pulley 5.

The drive belt 31 further has a third engaging portion 31d held in engagement with the drive pulley 9 and formed with an adjusting hole 31c having an inner diameter large sufficient to receive the adjusting screw 32. The adjusting screw 32 is received in the third hole 31c of the drive belt 31 and rotated to allow the length 33 of the drive belt 31 to be adjusted between the driven pulley 5 and the drive pulley 9 under the state that the first hole 31b and the second hole 31a are respectively held in engagement with the drive pulley 9 and the driven pulley 5.

The length adjusting means 30 facilitates to adjust the circumferential length of the looped drive belt 31 in proportion to the distance between the driven pulley 5 and the drive pulley 9 even in the case that the distance varies. The ultrasonic probe becomes more accurate and lower in the manufacturing cost.

Figure 5A:
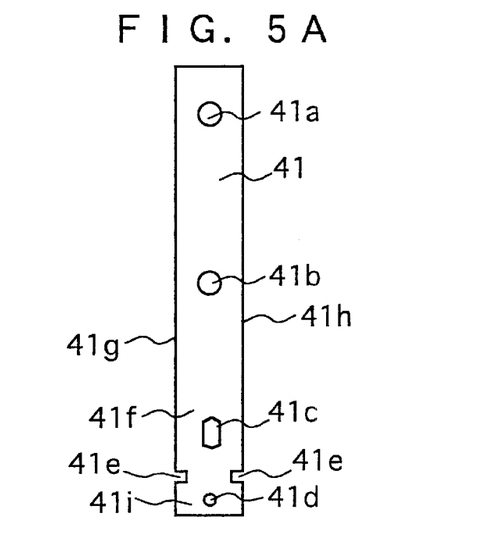
FIG. 5A is a plan view of a drive belt forming part of the fifth embodiment of the ultrasonic probe according to the present invention and held in the state being extended before being passed on the drive and driven pulleys.
Figure 5B:
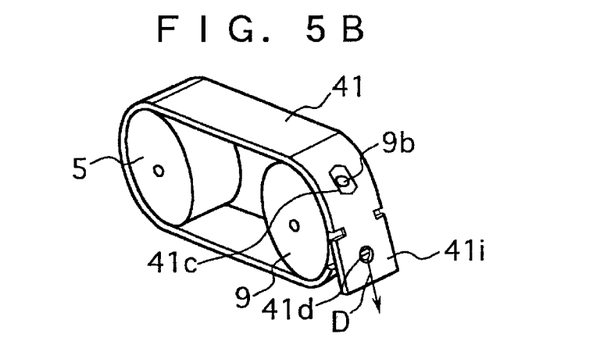
FIG. 5B is a perspective view of the drive belt shown in FIG. 5A but showing the drive belt in the state being passed on the drive and driven pulleys with a tension imparted to the drive belt.
Figure 5C:
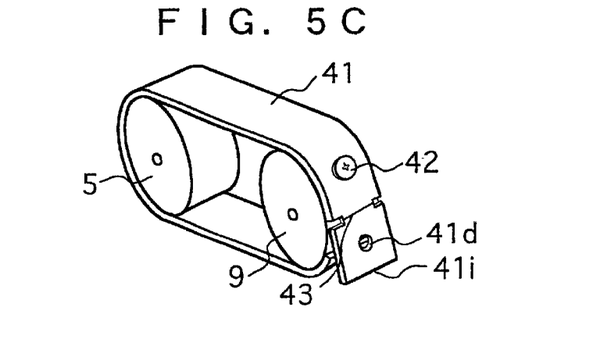
FIG. 5C is a perspective view similar to FIG. 5B but showing an adjusting screw screwed to the drive pulley.

Referring to FIGS. 5A to 5C of the drawings, there is shown a fifth preferred embodiment of the ultrasonic probe embodying the present invention. The ultrasonic probe of the present embodiment is similar in constitution to the first and fourth embodiments and thus includes elements the same in constitution and numerical reference as those of the ultrasonic probe of the first embodiment.

As shown in FIGS. 5A to 5C, the ultrasonic probe comprises length adjusting means 40 for adjusting lengths of both straightened portions of the drive belt 41, i.e. the distance between the driven pulley 5 and the drive pulley 9, with the first pulley 5 and the second pulley 9. The first projection 5a, not shown in FIGS. 5A to 5C, of the driven pulley 5 is received in the first hole 41b of the drive belt 41 to have the drive belt 41 wound onto and held in synchronized engagement with the driven pulley 5, while the second projection 9a, not shown in FIGS 5A to 5C, of the drive pulley 9 is received in the second hole 41a of the drive belt 41 to have the drive belt 41 wound onto and held in synchronized engagement with the drive pulley 9. The length adjusting means 40 further comprises an adjusting screw 42 operable to screw into the female screw 9b of the drive pulley 9.

The drive belt 41 is formed with an adjusting hole 41c similar in function but different in shape from the adjusting hole 31c of the drive belt 31 of the fourth embodiment. The adjusting hole 41c is substantially in the form of a rectangular shape having a length measured in the longitudinal direction of the drive belt 41 and a width measured in the direction perpendicular to the longitudinal direction of the drive belt 41. The length of the adjusting hole 41c is larger than the width of the adjusting hole 41c. The adjusting hole 41c has four corners. Preferably, each of the corners should be chamfered to avoid excessive stress to be placed on the corners.

The drive belt 41 has an extreme end tab 41i adjacent to the adjusting hole 41c. Between the adjusting hole 41c and the extreme end tab 41i of the drive belt 41, there are formed a pair of side notches 41e extending inwardly from the side surfaces 41g and 41h of the drive belt 41. The side notches 41e of the drive belt 41 are symmetrically formed with respect to the center line of the drive belt 41.

The extreme end tab 41i is formed with a fourth hole 41d which can be hooked by hooking implement to be pulled for imparting a tension to the drive belt 41.

The drive belt 10 while being driven by said drive pulley 9 is constantly imparted a tension at a tension level applied when the drive belt 10 is assembled with the first and second pulleys 5 and 9.

The description will be hereinafter directed to a method according to the present invention. The method is performed for fabricating the aforesaid ultrasonic probe through the following steps, especially for winding the drive belt 41 onto the driven pulley 5 and the drive pulley 9 and for imparting a tension to the drive belt 41.

The driven shaft 2, the transducer 1 supported by said driven shaft 2, the drive shaft 7, the adjusting screw 42 and the drive belt 41 are at first prepared. As aforesaid, the drive belt 41 has first and second holes 41a and 41b respectively constituting first and second engaging portions, and third engaging portion 41f formed with an adjusting hole 41c and an extreme end tab 41i.

The drive shaft 7 is then arranged in parallel and spaced relationship with the driven shaft 2.

Following the above preparing step, the drive belt 41 is wound onto the drive pulley 9 and the driven pulley 5 to have the first and second engaging portions 41a and 41b held in engagement with said drive pulley 9 and said driven pulley 5, respectively.

The drive belt 41 is then screwed to said drive pulley 9 by the adjusting screw 42 through the adjusting hole 41c of the drive belt 41.

During or before the screwing step, the drive belt 41 wound onto the drive pulley 9 and the driven pulley 2 is imparted a tension slightly exceeding a predetermined tension level by pulling the extreme end tab 41i in the longitudinal direction, shown by an arrow D in FIG. 5B, of the drive belt 41. In this tension imparting step, the predetermined tension level is set at a tension sufficient to drive the transducer 1 through the drive belt 41. The adjusting screw 42 is then put into the female screw 9b as shown in FIG. 5C and tightened up under the condition that the predetermined tension is imparted to the drive belt 41. At this time, the third engaging portion 41f of the drive belt 41 is securely mounted to the drive pulley 9 in conjunction with the adjusting screw 42.

The extreme end tab 41i is then cut off along a line 43 depicted in FIG. 5c and separated from the drive belt 41.

In the above manufacturing method according to the present invention, the tension imparting step eliminates the need for installing an additional tension imparting mechanism including the earlier mentioned idler roller and the like because of the fact that the drive belt 41 is tightened and imparted a tension at a predetermined level sufficient to drive the transducer 1 before the adjusting screw 42 is put into the female screw 9b, thereby reducing the number of parts forming part of the tension imparting mechanism. Furthermore, the drive belt 41 wound onto the drive pulley 9 and the driven pulley 2 imparted a tension slightly exceeding the predetermined tension level increases the accuracy of the ultrasonic probe. This leads to the fact that the above mentioned manufacturing method makes it possible to manufacture the ultrasonic probe less costly and more reliable then the conventional manufacturing method.

Figure 6A:
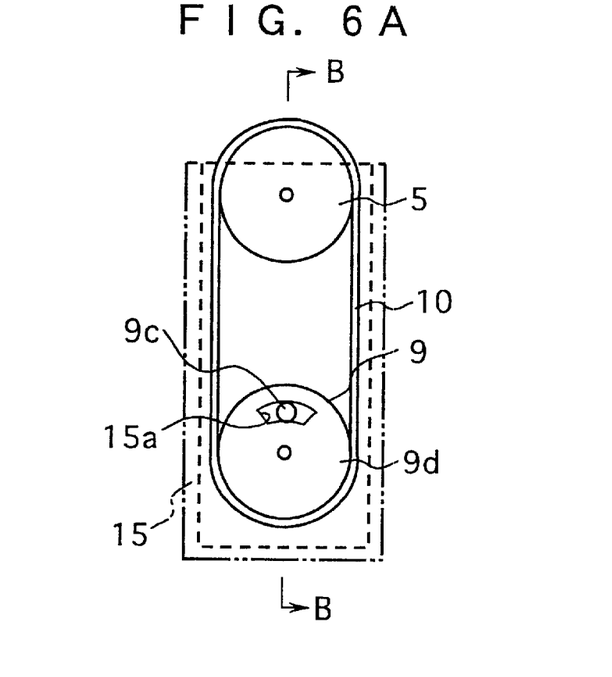
FIG. 6A is a front view of a loop belt and the drive and driven pulleys forming part of the sixth embodiment of the ultrasonic probe according to the present invention.
Figure 6B:
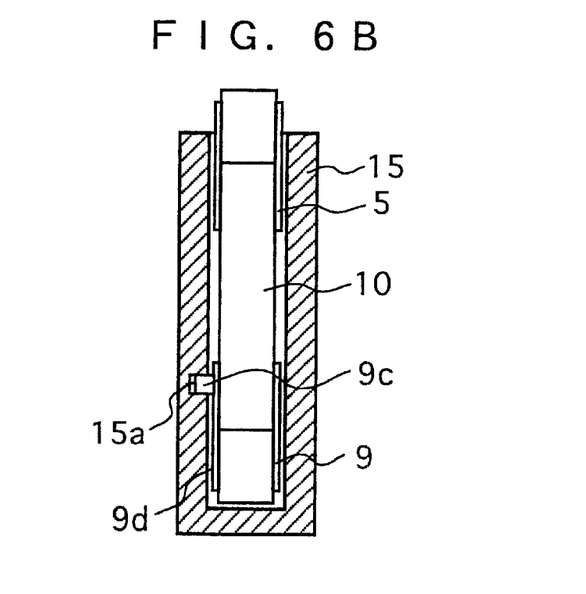
FIG. 6B is a fragmentary cross-sectional view taken along the line B—B of FIG. 6A.

FIGS. 6A and 6B in combination show a sixth preferred embodiment of the ultrasonic probe embodying the present invention. The ultrasonic probe of the present embodiment is similar in constitution to the first embodiment and thus includes elements the same in constitution and numerical reference as those of the ultrasonic probe of the first embodiment. FIG. 6A is a front elevation of the present embodiment, and FIG. 6B is a side view of the present embodiment.

The ultrasonic probe comprises rotation restricting means for restricting the rotation of the drive pulley 9 to within an allowable rotation range. As shown in FIGS. 6A and 6B, the drive pulley 9 has a cylindrical stop projection 9c projecting from one side surface 9d of the drive pulley 9, while the inner case 15 is formed with a groove 15a having the stop projection 9c of the drive pulley 9 received therein to ensure that the drive pulley 9 is allowed to rotate within the allowable rotation range. The groove 15a of the inner case 15 is for example formed in an arcuate shape having both ends for stoppers.

The description will be hereinafter directed to the operation of the above present embodiment.

Figure 7A:
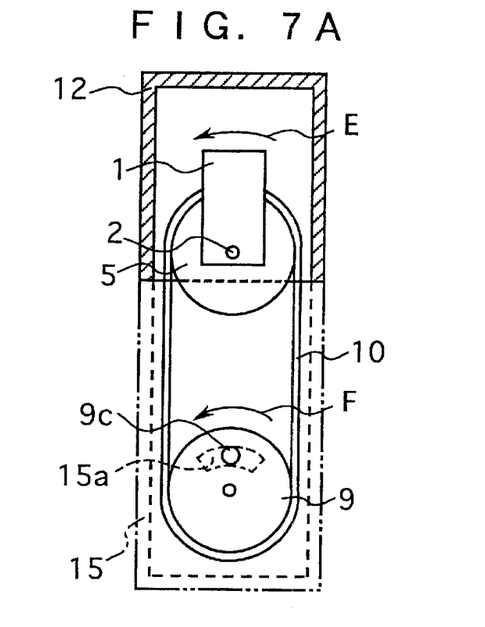
FIG. 7A is a side view, partly cross-sectioned, of a transducer, a loop belt, the drive and driven pulleys and a partly sectioned inner case collectively forming the seventh embodiment of the ultrasonic probe according to the present invention.

As shown in FIG. 7A, the transducer 1 connected with the driven pulley 5 through the driven shaft 2 is driven in a rotational direction shown by an arrow E when the drive pulley 9 is driven to rotate a rotational direction shown by an arrow F.

Figure 7B:
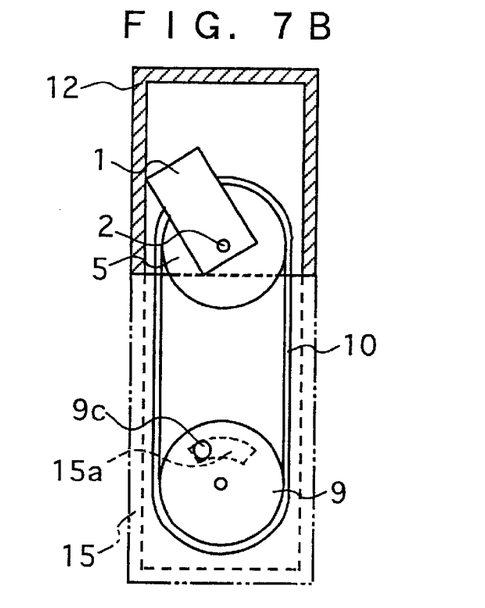
FIG. 7B is a side view, partly cross-sectioned, of the transducer, the drive belt, the driven and drive pulleys and an inner case forming part of the seventh embodiment of the ultrasonic probe according to the present invention.

As shown in FIG. 7B, the stop projection 9c of the drive pulley 9 is brought into contact with the end stopper of the groove 15a of the inner case 15 and stopped even when the rotation position of the drive motor 6 exceeds over one of predetermined limit positions adjacent to the both end stoppers of the groove 15a. The end stopper of the groove 15a of the inner case 15 prevents any force exceeding the driving torque of the drive motor 6 from being loaded on the drive belt 10. The drive belt 10 is shown in FIG. 7A and FIG. 7B may be any other types such as an endless flat strip belt according to the present invention. The excessive force loaded on the drive belt 10 causes wear and tear of the drive belt 10 and deteriorates the reliability of the ultrasonic probe. The ultrasonic probe thus constructed reduces the wear and tear of the drive belt 10 thereby ensuring a high degree of reliability.

Figure 8:
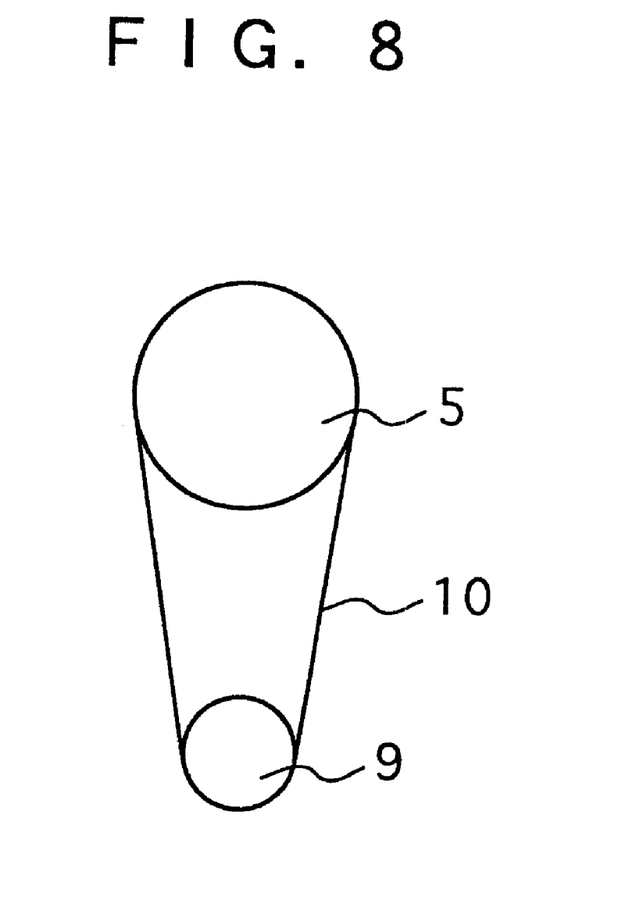
FIG. 8 is a schematic side view of a loop belt and the drive and driven pulleys forming part of the eighth embodiment of the ultrasonic probe according to the present invention.

Referring to FIG. 8 of the drawings, there is shown a seventh preferred embodiment of the ultrasonic probe embodying the present invention. The ultrasonic probe therein disclosed is similar in constitution to the ultrasonic probe disclosed by the first embodiment and thus includes parts and elements the same in constitution and bearing numerical references the same as those of the ultrasonic probe of the first embodiment except for the following parts and elements.

In the seventh embodiment, the driven pulley 5 has a relatively large diameter Da, while the drive pulley 9 has a relatively small diameter Db smaller than that of the driven pulley 5. In the case that the load torque T1 is applied to the drive belt 10, the driving torque Td required to drive the drive pulley 9 is determined by the equation (1) as follows.

$$Td=(Db/Da)T1 \quad (1)$$

It will be understood from the above mentioned equation that the driving torque Td becomes smaller than the load torque T1 due to the fact that the diameter Da the driven pulley Db is larger than the diameter Db of the drive pulley 9.

The ultrasonic probe exemplified by the seventh embodiment makes it possible to utilize a drive motor smaller than that of the conventional ultrasonic probe, thereby providing a less expensive and more compact ultrasonic probe than the conventional ultrasonic probe. This is because the diameter Da of the driven pulley 5 is set to be larger than the diameter Db of the drive pulley 9 with the driving torque "Td" at a smaller value.

According to the present invention, the ultrasonic probe thus constructed makes it possible to reduce the rotation radius of the transducer independently of the size of the electric motor by spacing the rotation axes of the drive motor and the transducer, and is therefore possible to provide an ultrasonic probe smaller in size than the conventional ultrasonic probe. Further, the ultrasonic probe is prevented from deteriorating in accuracy because the rotation of the drive motor is transferred into the rotational motion of the transducer without causing a backlash.

The present invention has thus been shown and described above with reference to specific embodiments, however, it should be noted that the invention is not limited to the details of the illustrated structures but changes and modifications may be made without departing from the scope of the appended claims.

What is claimed is:

1. An ultrasonic probe, comprising:
   a housing including an outer case and an inner case accommodated in and partly connected to said outer case and held stationary with respect to said outer case;
   a driven shaft rotatably supported by said inner case of said housing;
   a transducer supported by said driven shaft to be swingable on one side of said driven shaft and operative to transduce an electric signal to and from an ultrasound, said transducer having said ultrasound emitted therefrom and reflected thereto through said housing in a predetermined direction;
   a drive shaft rotatable supported by said inner case of said housing spaced apart from and in parallel relationship with said driven shaft in said predetermined direction;
   a drive motor supported on said inner case of said housing and drivably connected to said drive shaft; and
   a drive belt intervening between said driven shaft and said drive shaft to transmit the rotation from said drive motor to said transducer.

2. An ultrasonic probe as set forth in claim 1, in which said drive belt is substantially in the form of a loop shape and has rectangular cross section.

3. An ultrasonic probe as set forth in claim 1, which further comprises:
   a driven pulley fixedly supported on said driven shaft of said transducer and rotatable together with said driven shaft; and
   a drive pulley fixedly supported on said drive shaft and rotatable together with said drive shaft, said drive belt being passed on said driven pulley and said drive pulley.

4. An ultrasonic probe as set forth in claim 3, which further comprises synchronizing means for synchronizing said driven pulley with said drive pulley when said driven pulley is driven to rotate by said drive pulley through said drive belt.

5. An ultrasonic probe as set forth in claim 4, in which said synchronizing means is constituted by a first projection formed on said driven pulley to radially project from the outer peripheral surface of said driven pulley, a second projection formed on said drive pulley to radially project from the outer peripheral surface of said drive pulley, and said drive belt respectively having first and second holes formed therein in spaced apart relationship with each other in the rotation direction of said drive belt, said first and second holes respectively having said first and second projections received therein to ensure that said driven pulley is driven to rotate in synchronism with said drive pulley.

6. An ultrasonic probe as set forth in claim 3, which further comprises length adjusting means for adjusting the length of said drive belt between said first pulley and said second pulley.

7. An ultrasonic probe as set forth in claim 6, which further comprises an adjusting screw, and in which said drive belt has a first engaging portion held in engagement with said drive pulley, a second engaging portion held in engagement with said driven pulley and a third engaging portion held in engagement with said drive pulley and formed with an adjusting hole having an inner diameter large enough to receive therein said adjusting screw to ensure that said drive belt is adjusted in length under the state that said first engaging portion and said second engaging portion are respectively held in engagement with said drive pulley and said driven pulley, said length adjusting means being constituted by said adjusting screw, said drive belt, said drive pulley and said driven pulley.

8. An ultrasonic probe as set forth in claim 7, in which said adjusting hole is in the form of a rectangular shape having a length measured in the longitudinal direction of said drive belt and a width measured in the direction perpendicular to the longitudinal direction of said drive belt, said length is larger than said width.

9. An ultrasonic probe as set forth in claim 8, in which said drive belt has an extreme end tab adjacent to said adjusting hole and formed with a pair of side notches extending inwardly from the side surfaces of said drive belt between said adjusting hole and said extreme end tab of said drive belt and symmetrically formed with respect to the center line of said drive belt.

10. An ultrasonic probe as set forth in claim 3, which further comprises rotation restricting means for restricting the rotation of said drive pulley to within an allowable rotation range.

11. An ultrasonic probe as set forth in claim 10, which said drive pulley has a stop projection projecting from one side surface of said drive pulley, said inner case being formed with a groove having said stop projection received therein to ensure that said drive pulley is allowed to rotate within said allowable rotation range.

12. An ultrasonic probe as set forth in claim 3, in which the outer diameter of said driven pulley is larger than that of said drive pulley.

13. An ultrasonic probe as set forth in claim 3, which further comprises tension imparting means for imparting tension to said drive belt.

14. An ultrasonic probe as set forth in claim 13, in which said tension imparting means comprises a swingable arm having one end portion pivotably supported on said inner case to be swingable with respect to said inner case and the other end portion bent toward said drive belt, an idler roller rotatably supported on the other end portion of said swingable arm in pressing contact with said drive belt, and resilient means for resiliently urging said idler roller into pressing contact with said drive belt to have said drive belt maintained under its tensioned state.

15. An ultrasonic probe as set forth in claim 14, in which said resilient means is constituted by a helical coil spring having one end connected to the longitudinally intermediate portion of said swingable arm and the other end connected to said inner case to ensure that said idler roller is held in pressing contact with said drive belt to have said drive belt maintained under its tensioned state.

16. An ultrasonic probe as set forth in claim 13, in which said drive belt while being driven by said drive pulley is constantly imparted a tension at a tension level applied when said drive belt is assembled with said first and second pulleys.

17. A method of producing an ultrasonic probe, comprising the steps of:
 preparing a driven shaft, a transducer supported by said driven shaft, a drive shaft arranged in parallel to said driven shaft and spaced apart from said driven shaft, an adjusting screw and a drive belt having first and second engaging portions, third engaging portion formed with an adjusting hole and an extreme end tab;
 winding said drive belt onto said drive pulley and said driven pulley to have said first and second engaging portions held in engagement with said drive pulley and said driven pulley;
 screwing said drive belt to said drive pulley by said adjusting screw through said adjusting hole of said drive belt;
 imparting said drive belt wound onto said drive pulley and said driven pulley a tension at a predetermined level by pulling said extreme end tab in the longitudinal direction of said drive belt until said third engaging portion of said drive belt is screwed to said drive pulley; and
 cutting and separating said extreme end tab from said drive belt.

\* \* \* \* \*

UNITED STATES PATENT AND TRADEMARK OFFICE
CERTIFICATE OF CORRECTION

PATENT NO. : 6,569,100 B2
DATED : May 27, 2003
INVENTOR(S) : Eiichi Okawa et al.

It is certified that error appears in the above-identified patent and that said Letters Patent is hereby corrected as shown below:

Column 12,
Line 41, please delete "shaft rotatable support", and insert therefor -- shaft rotatably supported --.

Signed and Sealed this

Twenty-first Day of October, 2003

JAMES E. ROGAN
*Director of the United States Patent and Trademark Office*